(12) United States Patent
Pabst et al.

(10) Patent No.: US 12,279,379 B2
(45) Date of Patent: Apr. 15, 2025

(54) AUTOCLAVABLE ELECTRONICS UNIT FOR AN ENDOSCOPE, METHOD FOR PRODUCING AN AUTOCLAVABLE ELECTRONICS UNIT AND ENDOSCOPE

(71) Applicant: OLYMPUS WINTER & IBE GMBH, Hamburg (DE)

(72) Inventors: Sven Pabst, Giekau (DE); Sebastian Jungbauer, Hamburg (DE)

(73) Assignee: OLYMPUS WINTER & IBE & GMBH, Hamburg (DE)

( * ) Notice: Subject to any disclaimer, the term of this patent is extended or adjusted under 35 U.S.C. 154(b) by 893 days.

(21) Appl. No.: 17/399,154

(22) Filed: Aug. 11, 2021

(65) Prior Publication Data

US 2021/0378104 A1 Dec. 2, 2021

Related U.S. Application Data

(63) Continuation of application No. PCT/EP2020/052733, filed on Feb. 4, 2020.

(30) Foreign Application Priority Data

Feb. 11, 2019 (DE) .......................... 102019103290.3

(51) Int. Cl.
*H05K 1/00* (2006.01)
*A61B 1/00* (2006.01)
(Continued)

(52) U.S. Cl.
CPC ............ *H05K 3/284* (2013.01); *A61B 1/0011* (2013.01); *H05K 1/0281* (2013.01); *H05K 1/0298* (2013.01); *H05K 2201/10106* (2013.01)

(58) Field of Classification Search
CPC .......... H05K 1/00; H05K 1/02; H05K 1/0216; H05K 1/0218; H05K 1/0225;
(Continued)

(56) References Cited

U.S. PATENT DOCUMENTS 4,793,616 A * 12/1988 Fernandez ........... A63B 53/047
473/347
5,418,566 A * 5/1995 Kameishi ............... A61B 1/051
348/340
(Continued)

FOREIGN PATENT DOCUMENTS

DE 69930110 T2 9/2006
DE 102008025938 A1 12/2009
(Continued)

OTHER PUBLICATIONS

Fine Line Gesellschaft fur Leiterplattentechnik mbH:, Rigid-Flex, Flex und Semi-Flex Leiterplatten. Edition Mar. 17, 2017, Vers. 1.1., Hilden, 2017, pp. 1-89—company publication.
(Continued)

*Primary Examiner* — Xiaoliang Chen
(74) *Attorney, Agent, or Firm* — Scully, Scott, Murphy & Presser, P.C.

(57) ABSTRACT

An autoclavable electronics unit for an endoscope, the autoclavable electronics unit including: a multi-layer printed circuit board having a rigid region and a flexible region, the rigid region being reinforced by stiffener material to have a greater rigidity than the flexible region and the flexible region is configured to be bendable. Where the multi-layer printed circuit board is formed from structured layers made of conductive and non-conductive materials adhered together, in which the conductive structures form conductor
(Continued)

tracks and contact surfaces; the rigid region is provided with one or more electronic components; and the rigid region is covered by an epoxy resin.

15 Claims, 1 Drawing Sheet

(51) Int. Cl.
 H05K 1/02 (2006.01)
 H05K 1/09 (2006.01)
 H05K 3/02 (2006.01)
 H05K 3/06 (2006.01)
 H05K 3/10 (2006.01)
 H05K 3/28 (2006.01)
 H05K 3/36 (2006.01)

(58) Field of Classification Search
 CPC .. H05K 1/0274; H05K 1/0277; H05K 1/0278; H05K 1/028; H05K 1/0281; H05K 1/0298; H05K 1/09; H05K 1/118; H05K 1/144; H05K 1/181; H05K 3/02; H05K 3/027; H05K 3/0026; H05K 3/0058; H05K 3/0064; H05K 3/06; H05K 3/10; H05K 3/36; H05K 3/284; H05K 3/285; H05K 3/361; H05K 3/363; H05K 3/4611; H05K 3/4623; H05K 3/4638; H05K 3/4644; H05K 3/4652; H05K 3/4691; H05K 2201/10106; A61B 1/0011; A61B 1/042; A61B 1/051
 USPC ........ 361/749, 264, 748, 803; 174/258, 259, 174/260, 261, 262; 348/65, 294, 340; 427/58, 74, 98.5, 331, 340, 387, 487
 See application file for complete search history.

(56) References Cited

U.S. PATENT DOCUMENTS

| | | | |
|---|---|---|---|
| 6,274,939 B1 | 8/2001 | Wolf | |
| 6,966,482 B2* | 11/2005 | Totani | H05K 3/363 257/734 |
| 7,348,492 B1* | 3/2008 | Kawai | H05K 3/361 174/254 |
| 8,238,109 B2* | 8/2012 | Sagisaka | H05K 3/4691 361/748 |
| 10,181,446 B2* | 1/2019 | Dobashi | H04N 23/00 |
| 10,356,903 B1* | 7/2019 | Chen | H05K 1/144 |
| 10,368,445 B2* | 7/2019 | Lee | H05K 1/09 |
| 2003/0143408 A1* | 7/2003 | Benayoun | C08J 3/03 428/447 |
| 2004/0112632 A1* | 6/2004 | Michiwaki | H05K 3/4691 174/254 |
| 2007/0012475 A1* | 1/2007 | Kawaguchi | H05K 3/361 29/830 |
| 2007/0013041 A1* | 1/2007 | Ishigaki | H05K 3/4691 257/686 |
| 2008/0079887 A1* | 4/2008 | Liu | G02F 1/136286 349/149 |
| 2008/0289859 A1* | 11/2008 | Mikado | H05K 3/4691 427/98.5 |
| 2009/0028497 A1* | 1/2009 | Kodama | H05K 1/0274 29/831 |
| 2010/0065313 A1* | 3/2010 | Takeuchi | H05K 1/0278 174/258 |
| 2010/0140730 A1 | 6/2010 | Soloviev et al. | |
| 2012/0164335 A1* | 6/2012 | Maliverney | C08J 7/05 427/342 |
| 2012/0181068 A1* | 7/2012 | Kato | H05K 3/44 156/60 |
| 2012/0186860 A1* | 7/2012 | Takaoka | H05K 1/028 174/254 |
| 2012/0253698 A1* | 10/2012 | Cokonaj | B06B 1/0622 702/39 |
| 2013/0269183 A1* | 10/2013 | Vesce | H05K 3/4623 29/830 |
| 2013/0292050 A1* | 11/2013 | Chiou | H05K 3/4691 156/252 |
| 2013/0292164 A1* | 11/2013 | Park | H05K 3/10 29/846 |
| 2015/0114689 A1* | 4/2015 | Ishihara | H05K 3/4691 156/247 |
| 2015/0200317 A1* | 7/2015 | Kretschmann | C09D 183/14 428/447 |
| 2016/0057873 A1* | 2/2016 | Richardson | H05K 1/0216 361/749 |
| 2016/0066429 A1* | 3/2016 | Taniguchi | H05K 1/0281 361/749 |
| 2016/0154173 A1* | 6/2016 | Lee | H01L 33/641 257/91 |
| 2016/0345431 A1* | 11/2016 | Lee | H05K 1/0278 |
| 2017/0027055 A1* | 1/2017 | Lee | H05K 3/4691 |
| 2017/0118833 A1* | 4/2017 | Lee | H05K 1/09 |
| 2018/0020131 A1* | 1/2018 | Zhao | H04N 23/55 |
| 2018/0178034 A1* | 6/2018 | Iguchi | A61N 5/0616 |
| 2018/0249049 A1* | 8/2018 | Maeda | H04N 23/54 |
| 2019/0306993 A1* | 10/2019 | Kim | B32B 15/20 |
| 2019/0337446 A1* | 11/2019 | Salter | F21S 41/50 |
| 2019/0349507 A1* | 11/2019 | Lee | H04N 23/54 |
| 2020/0066693 A1* | 2/2020 | Kim | H05K 1/02 |
| 2020/0219919 A1* | 7/2020 | Tanaka | H04N 23/54 |
| 2020/0260011 A1* | 8/2020 | Sasaki | G03B 5/00 |
| 2021/0038436 A1* | 2/2021 | Kieswetter | A61B 17/322 |

FOREIGN PATENT DOCUMENTS

| | | |
|---|---|---|
| DE | 102009044199 A1 | 6/2010 |
| EP | 2915477 A1 | 9/2015 |
| JP | 2011-050545 A | 3/2011 |
| WO | 2017/040692 A1 | 3/2017 |
| WO | 2018/158897 A1 | 9/2018 |

OTHER PUBLICATIONS

International Search Report dated Apr. 23, 2020 issued in PCT/EP2020/052733.

* cited by examiner

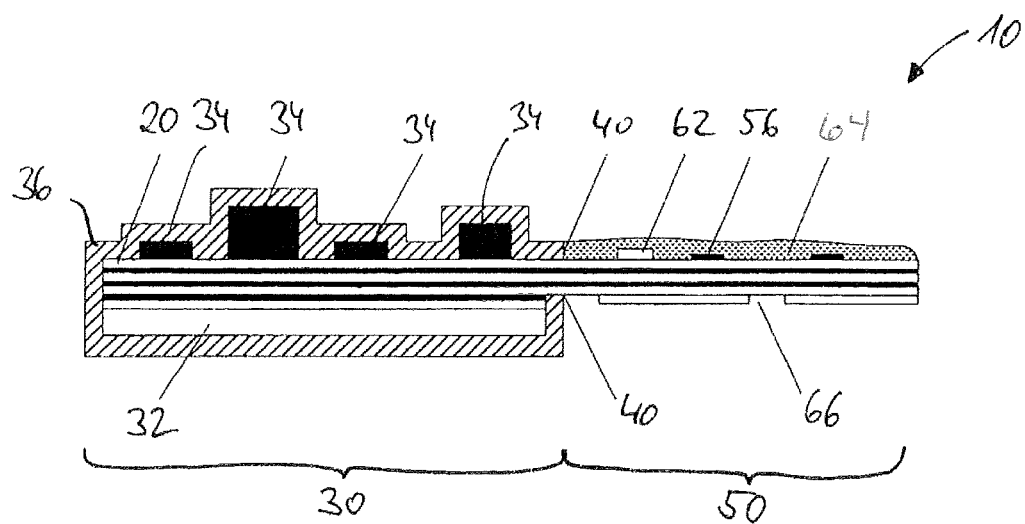
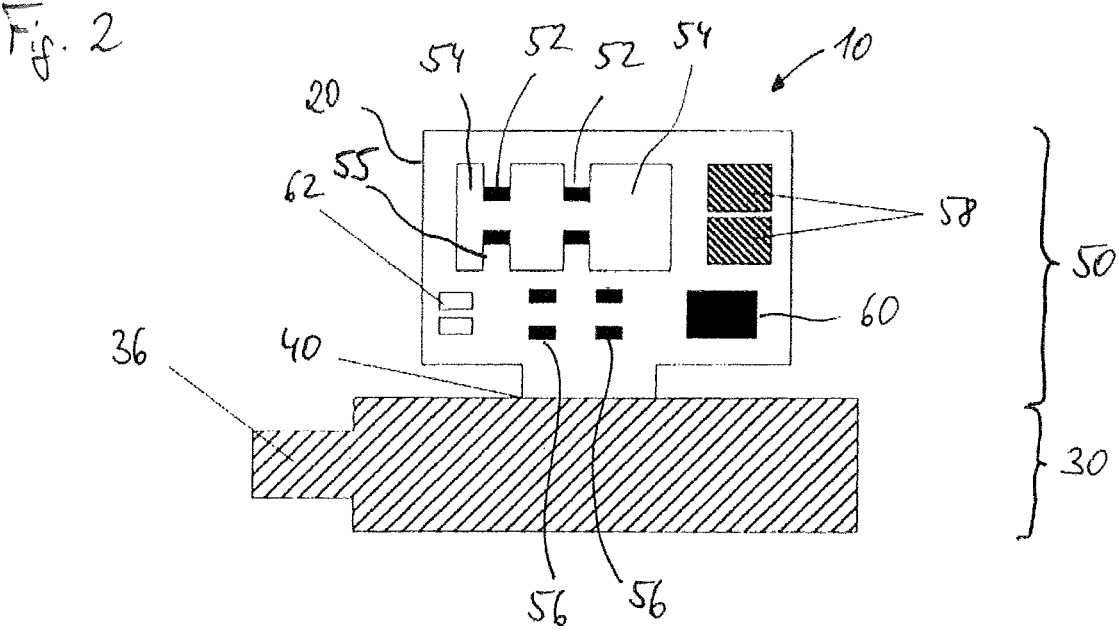

AUTOCLAVABLE ELECTRONICS UNIT FOR AN ENDOSCOPE, METHOD FOR PRODUCING AN AUTOCLAVABLE ELECTRONICS UNIT AND ENDOSCOPE

CROSS-REFERENCE TO RELATED APPLICATION

The present application is a continuation of PCT/EP2020/052733 filed on Feb. 4, 2020, which is based upon and claims the benefit to DE 10 2019 103 290.3 filed on Feb. 11, 2019, the entire contents of each of which are incorporated herein by reference.

BACKGROUND

Field

The present disclosure relates to an autoclavable electronics unit for an endoscope, a method for producing an autoclavable electronics unit and an endoscope.

Prior Art

Surgical endoscopes, such as video endoscopes, are autoclaved, i. e., cleaned and sterilized, in autoclaves after each application. This takes place with application of hot water and rinsing fluid, for example hot vapor and overpressure or underpressure. This means that the optical and electronic systems of the endoscope are also exposed to high temperatures and moisture, against which they must be protected in order to maintain their functionality even under overpressure and underpressure after frequently repeated uses and cleaning cycles.

A part of the electronics unit in an endoscope is therefore accommodated in hermetically sealed parts of the endoscope such that this part of the electronics unit, together with parts of the optical and mechanical systems of an endoscope, are protected against ingress of moisture. Other parts of the endoscope, such as parts of the handle at the proximal end of the endoscope, however, are so-called "non-hermetic spaces" into which moisture can enter during autoclaving. Provided that an electronics unit is to be used in the non-hermetic space of the endoscope, such unit must be protected accordingly against the effects of the cleaning or respectively sterilization.

With the endoscopes distributed by the applicant, the electronics unit which is arranged in the non-hermetic space can be based on rigid FR4 printed circuit boards (PCBs). The electronic components mounted thereon are provided with a sheet metal housing which is filled with a silicone material in order to protect the circuit against moisture. The casting process is very time consuming in this case. Moreover, the metal housing is not an electrical insulator. Due to the construction with a housing, a larger installation space is used, which would have to be made even larger for an insulating housing material, since for example PEEK, which would be a potential housing material, cannot be produced with walls as thin as those made from steel.

SUMMARY

An object is to provide an electronics unit suitable for use in the non-hermetic part of an endoscope, a method for the production of such a unit, and a corresponding endoscope, with which the disadvantages described above are avoided.

Such object can be achieved by an autoclavable electronics unit for an endow scope, comprising a multi-layer printed circuit board, which, in a rigid region, is reinforced by means of an additional stiffener, such as a stiffening plate or one or more stiffening layers and, in a flexible region, is configured to be bendable, wherein the multi-layer printed circuit board is formed from structured layers made of conductive and non-conductive materials adhered together, in which the conductive structures form conductor tracks and contact surfaces, wherein the rigid region is equipped with electronic components and covered by an epoxy resin, such as filled with a ceramic powder.

Instead of rigid FR4 printed circuit boards, thus printed circuit boards that are flexible in principle can be used, which are partially reinforced in order to receive electronic components, and remain flexible in other regions in order to be installed in the available installation space in the non-hermetic part of an endoscope, for example a handle. The sealing of the electronic components can be implemented separately for the flexible and the rigid region, wherein the rigid region can be coated with an epoxy resin which itself, particularly after curing, has a high viscosity or inflexibility whereas the flexible part is kept free thereof. Due to the coating with the epoxy resin, an individual housing may not be needed so that installation space can be saved. Additionally, the epoxy material is an electrical insulator. The flexible part of the printed circuit board does not receive any electronic components but instead serves to establish contact with conductors and further printed circuit boards.

The epoxy resin can be filled with a ceramic powder in an embodiment, such that, in terms of its thermal and mechanical properties, the material is adapted to the housing of the electronic components that are arranged on the rigid part of the flexible printed circuit board. In this context, a material and method for applying the material by TURCK-Duotec, Delemont, Switzerland, can be used, which provides an autoclaving-resistant seal.

In embodiments, the covering of the rigid region with the electronic components can be produced by injecting or casting the epoxy resin around it, wherein the covering of the electronic components can have a homogeneous layer thickness. The injection molding method of the company TURCK-Duotec mentioned above generates such an outer contour of the injected material following the topography of the electronic components such that a homogeneous layer thickness forms.

In one embodiment, the flexible region of the printed circuit board can be guided out of the rigid region covered by the epoxy resin via a feedthrough with a width that is reduced compared to the width of the rigid region. The reduction of the width of the feedthrough compared to the width of the rigid region can ensure that the feedthrough is configured in a tapered manner and has a small cross-section so that little diffusion surface is available for moisture, particularly water vapor.

In embodiments, the flexible region of the printed circuit board can comprise one or more nominal bending points with reduced thickness. The nominal bending points can provide the flexible part of the printed circuit board with a defined shape. For example, the nominal bending points can be configured as straight lines that are arranged in parallel with one another. Such a configuration allows for rolling the flexible part such that the autoclavable electronics unit can be fitted for example into the hollow cylindrical space in the handle of the endoscope.

In embodiments, the flexible region of the printed circuit board can comprise soldered contact points that are or can be connected to cables and/or one or more further printed circuit boards. Such soldered contact points can be arranged away from nominal bending points, wherein an arrangement in a part with an increased stiffness compared to the nominal bending points of the flexible part is favorable for the permanence of soldered contacts. Additional metal surfaces can, for example, be used for a serial number to be applied in clear text or as a carrier of a two-dimensional code applied by means of laser labelling.

In one embodiment, the flexible region of the printed circuit board and, if applicable, the feedthrough to the rigid region can be sealed with a silicone material, such as at least a partially transparent silicone material, wherein the seal sealingly adjoins the covering of the rigid region with the epoxy resin or partially overlaps such region sealingly. Conversely to the epoxy resin, the silicone material itself is flexible so that the seal of the flexible part of the printed circuit board is ensured even when the flexible part of the printed circuit board is bent in order to be fitted into the non-hermetic space of an endoscope. In an embodiment, if the flexible region of the printed circuit board can be equipped with one or more LEDs for signal transmission, a transparent silicone material can be used for sealing.

In a further embodiment, the flexible region of the printed circuit board can be equipped with an electrical contact point for a digital, such as a serial, interface. For example, a UART signal can be tapped on the contact surface or contact point. Status information of the electronics unit can be read out by means of the LED or LEDs and/or the digital interfaces during the assembly despite the opaque coating of the electronic components on the rigid part of the printed circuit board, which is advantageous for the quality inspection.

As a result of the autoclave process, moisture can collect in the printed circuit board to an increased degree, which results in parasitic resistances forming between adjacent conductor tracks. This can have a distorting effect, such as with analogous measuring stations with high input resistances. For this reason, the distances between conductor tracks of sensitive signals can be selected to be particularly large in embodiments. Furthermore, to improve the quality of the electronic signal transmission, in embodiments, at least part of the conductor tracks can be enclosed with shielding structures, such as protective rings or U-shaped structures, which are associated particularly with low-interference signals. For example, the grounding terminal is such a low-interference or non-critical signal.

Such object can also be achieved by a method for producing a previously described autoclavable electronics unit for an endoscope, the method comprising:
  a) Producing a flexible, multi-layer printed circuit board from structured layers of conductive and non-conductive materials adhered together in which the conductive structures form conductor tracks and contact surfaces,
  b) Producing a rigid region of the flexible printed circuit board by reinforcing the rigid region with an additional stiffening plate or one or more stiffening layers, wherein a flexible region of the flexible printed circuit board remains unreinforced,
  c) Equipping the rigid region of the printed circuit board with electronic components,
  d) Covering the rigid region with an epoxy resin, such as an epoxy resin filled with ceramic powder.

With this method, a previously described autoclavable electronics unit is provided, such that the method can have the same features, properties, and advantages as the autoclavable electronics unit. The explanations given with regard to the autoclavable electronics unit and its embodiments apply accordingly to the method, as well.

In step d), the epoxy resin can be injected or cast to surround the rigid region in one embodiment of the method.

In one embodiment, a flexible region of the printed circuit board can be connected to a further printed circuit board via soldered contact points.

A fully tight seal can be produced in one embodiment of the method in that a or the flexible region of the printed circuit board can be sealed with at least partially transparent, silicone material, wherein the seal sealingly adjoins the covering of the rigid region with the epoxy resin or partially overlaps the latter sealingly. In this manner, the rigid and flexible parts of the printed circuit board are each provided with a suitable coating which supports the rigidity or respectively flexibility of each portion.

The printed circuit board and the electronic components can be checked during the production of the autoclavable electronics unit for proper functioning by one or more optical or electronic interfaces arranged in the flexible region of the printed circuit board.

Moreover, such object can be achieved by an endoscope with an autoclavable electronics unit as previously described in a non-hermetic portion of the endoscope. The endoscope, too, can thus realizes the same features, properties, and advantages as the previously described autoclavable electronics unit.

BRIEF DESCRIPTION OF THE DRAWINGS

Further features will become evident from the description of embodiments, together with the claims and the appended drawings. Embodiments can fulfil individual features or a combination of multiple features.

The embodiments are described below, without restricting the general idea of the invention, based on exemplary embodiments in reference to the drawings, whereby we expressly refer to the drawings with regard to the disclosure of all details that are not explained in greater detail in the text. In the figures:

FIG. 1 illustrates a schematic sectional representation of an autoclavable electronics unit and FIG. 2 illustrates a schematic representation of a top view of an autoclavable electronics unit.

In the drawings, the same or similar elements and/or parts are, in each case, provided with the same reference numerals such that they are not introduced again in each case.

DETAILED DESCRIPTION

FIG. 1 is a schematic sectional representation of an autoclavable electronics unit 10. It is based on a multi-layer printed circuit board 20, the layers of which are represented as white and black layers. These different layers are connected to one another by means of an adhesive. The conductive structures form conductor tracks within the different layers. In some areas, the conductive structures are contacted through (not shown) between the layers so that a three-dimensional conductor track structure is formed. The printed circuit board 20 is in principle configured to be flexible, i. e., it can be rolled or bent, respectively.

In order to receive electronic components 34, a part of the printed circuit board 20 is reinforced by means of a stiffener 32 and thereby forms a rigid region 30. A further region of the printed circuit board 20 is not reinforced and thereby forms a flexible region 50. The flexible region 50 is not equipped with electronic components 34.

For sealing, at least the rigid region 30, such as an entirety of the rigid region 30, is coated with an epoxy resin covering 36 on one or both of the bottom side and the top side. For the application of the epoxy resin covering 36, an injection method was used which ensures that a homogeneous layer thickness of the epoxy resin covering 36 is achieved. To match the thermal and mechanical properties of the electronic components 34, it is useful to use a filled epoxy resin for the coating, which is filled with a ceramic powder that provides the epoxy resin with thermal and mechanical properties that are similar to those of the electronic components 34, so that stress cracking of the coating and lifting of the coating from the printed circuit board 20 do not occur even with repeated autoclaving under high temperatures.

In the flexible region 50, the thickness of the printed circuit board 20 is reduced compared to the thickness in the rigid region 30. This is apparent from the reduced number of layers in the multi-layer printed circuit board 20 compared to the number of layers in the rigid region 30. This further increases the flexibility of the flexible region 50 compared to the rigid region 30. In the flexible region 50, there are nominal bending points 66 on the bottom side of the printed circuit board 20, which are generated by reducing the layer thickness of a non-conductive material of the printed circuit board 20, and which represent especially flexible regions of the printed circuit board 20.

On the top side of the printed circuit board 20, an SMD (surface mounted device) LED 62 as well as a soldered contact point 56 are arranged in the flexible region 50. The top side of the printed circuit board 20 is provided with a silicone seal 64 in the flexible region 50. Such silicone seal is transparent, partially or in its entirety, such that optical signals from the LED can be viewed from the outside. The silicone seal 64 adjoins flush to the epoxy resin covering 36 or overlaps it partially. The bottom side of the printed circuit board 20 is not necessarily sealed with a silicone layer in the flexible region 50, since this side does not have any electrically conductive surfaces or electronic components to be protected.

FIG. 2 shows a schematic representation of a top view of an autoclavable electronics unit, which can correspond with the one from FIG. 1. The rigid region 30 is shown completely covered. A tapered feedthrough 40 is arranged between the printed circuit board 20 coated in the rigid region 30 and the not rigidly coated part of the printed circuit board 20 in the flexible region 50. The taper of the feedthrough 40 serves to reduce the contact surface for moisture during autoclaving so that the least possible amount of damaging moisture or other substances can enter through the feedthrough 40 into the intermediate space between the epoxy resin covering 36 and the printed circuit board 20.

In the flexible region 50 of the printed circuit board 20, the structures arranged on the top side of the printed circuit board 20 are apparent. Here, these are several soldered contact points 52, 56, LEDs 62, bare-metal surfaces 58, as well as a contact surface 60 for a serial interface.

The soldered contact points 52, of which there is a total of four in the example shown, serve to connect to a further printed circuit board. During bending of the flexible part and insertion in the non-hermetic part of an endoscope, such soldered points are exposed to high mechanical stresses. In order for these stresses not to result in the rupture of the soldered contacts, the soldered contact points 52 are each arranged at the ends of flexible arms 55, which are formed by shaping a recess 54 in the printed circuit board 20. Since the arms 55 are configured to be spring-loaded, the mechanical stress on the connecting soldered points themselves is reduced far enough for the connections to be robust. Further soldered contact points 56 serve to establish the connection with electrical cables the open ends of which are soldered to these points.

With the LEDs 62, as well as with the serial interface 60, signals from the electronics unit mounted in the rigid part 30 can be received, and in the case of the serial interface 60, can also be sent, which allow for diagnosing the electronics unit as well as the status of the conductor tracks of the printed circuit board 20.

The bare-metal surfaces 58 are used for identification and can, for example by means of a laser writing method, be labeled with a type number, serial number, or similar information.

A sealing of the flexible region 50 as well as of the feedthrough 40 with a silicone layer is implemented equally after completing the contacting of the soldered contact points 52, 56 to further printed circuit boards and/or electrical conductors.

The thus represented electronics unit 10 is protected against the influences of moisture, hot vapor, or other aggressive cleaning substances during autoclaving.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE SIGNS

10 Autoclavable electronics unit
20 Multi-layer printed circuit board
30 Rigid region
32 Stiffener
34 Electronic components
36 Epoxy resin covering
40 Feedthrough
50 Flexible region
52 Soldered contact point
54 Recess
55 Flexible arm
56 Soldered contact point
58 Bare-metal surfaces
60 Contact surface for serial interface
62 SMD LEDs
64 Silicone seal
66 Nominal bending point

What is claimed is:

1. An autoclavable electronics unit for an endoscope, the autoclavable electronics unit comprising:
   a multi-layer printed circuit board having a rigid region and a flexible region, the rigid region being reinforced by stiffener material to have a greater rigidity than the flexible region and the flexible region is configured to be bendable;
   wherein the multi-layer printed circuit board is formed from structured layers made of conductive and non-conductive materials adhered together, in which the conductive structures form conductor tracks and contact surfaces;
   the rigid region is provided with one or more electronic components;
   the rigid region is covered by an epoxy resin; and the flexible region is guided out of the rigid region via a feedthrough, the feedthrough having a width less than a width of the rigid region.

2. The autoclavable electronics unit for an endoscope according to claim 1, wherein the stiffener material is a stiffening plate or one or more stiffening layers.

3. The autoclavable electronics unit for an endoscope according to claim 1, wherein the resin contains a ceramic powder.

4. The autoclavable electronics unit for an endoscope according to claim 1, wherein the covering is produced by injecting or casting the epoxy resin around the rigid region.

5. The autoclavable electronics unit for an endoscope according to claim 4, wherein the covering has a homogeneous layer thickness.

6. The autoclavable electronics unit according to claim 1, wherein the flexible region comprises one or more nominal bending points having a thickness less than a thickness of other portions of the flexible region.

7. The autoclavable electronics unit according to claim 1, wherein the flexible region of the printed circuit board comprises one or more soldered contact points, each connected to one of a cable and another printed circuit board.

8. The autoclavable electronics unit according to claim 1, wherein the flexible region is covered by a seal formed of a silicone material, the seal sealingly adjoining the epoxy resin.

9. The autoclavable electronics unit according to claim 8, wherein the silicone material is at least partially transparent.

10. The autoclavable electronics unit according to claim 8, wherein the flexible region is guided out of the rigid region via a feedthrough, the seal further covering the feedthrough.

11. The autoclavable electronics unit according to claim 1, wherein the flexible region is provided with one or more LEDs for signal transmission.

12. The autoclavable electronics unit according to claim 1, wherein the flexible region is provided with an electrical contact point for a digital interface.

13. The autoclavable electronics unit according to claim 1, wherein at least part of the conductor tracks are enclosed with shielding structures.

14. The autoclavable electronics unit according to claim 13, wherein the shielding structures comprise one or more of protective rings or U-shaped structures.

15. An endoscope comprising the autoclavable electronics unit according to claim 1 disposed in a non-hermetic portion of the endoscope.

* * * * *